United States Patent [19]

Dessau et al.

[11] Patent Number: 4,822,942
[45] Date of Patent: Apr. 18, 1989

[54] STYRENE PRODUCTION

[75] Inventors: Ralph M. Dessau, Edison, N.J.; Ernest W. Valyocsik, Yardley, Pa.

[73] Assignee: Mobil Oil Corporation, New York, N.Y.

[21] Appl. No.: 214,781

[22] Filed: Jul. 1, 1988

Related U.S. Application Data

[63] Continuation of Ser. No. 138,473, Dec. 28, 1987, abandoned.

[51] Int. Cl.[4] .................. C07C 2/52; C07C 12/46
[52] U.S. Cl. .................................. 585/419; 585/435
[58] Field of Search .............................. 585/419, 435

[56] References Cited

U.S. PATENT DOCUMENTS

| | | | |
|---|---|---|---|
| 3,023,254 | 2/1962 | Othmer et al. | 585/419 |
| 3,702,293 | 11/1972 | Hayes et al. | 208/139 |
| 3,702,294 | 11/1972 | Rausch | 208/139 |
| 3,878,131 | 4/1973 | Hayes | 252/466 PT |
| 3,892,657 | 7/1975 | Wilhelm | 585/419 |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,652,360 | 3/1987 | Dessau | 208/138 |
| 4,699,708 | 10/1987 | Dessau | 208/111 |

FOREIGN PATENT DOCUMENTS

| | | | |
|---|---|---|---|
| 0107389 | 4/1984 | European Pat. Off. | |
| 552115 | 3/1943 | United Kingdom | 585/419 |
| 2033358 | 5/1980 | United Kingdom | |
| 2114150 | 8/1983 | United Kingdom | |

OTHER PUBLICATIONS

G. Wengui et al., "IR Study of Framework Vibrations and Surface Properties of High Silica Zeolites", Zeolites, Elsevir Science, Amsterdam, 1985, pp. 279–286.

Ione, Journal of Molecular Catalysis, 31, pp. 355–370, (1985).

Hongyuan et al., vol. 15, No. 7, (1986), Shiyou Huaqonq, pp. 405–410.

"Indium Oxide Treated H–ZSM–5 Catalyst, Properties and Catalytic Activity in the Methanol Conversion", Leon W. Zatorski, Bulletin of the Polish Academy of Sciences, Chemistry, vol. 35, No. 7–8, 1987.

*Primary Examiner*—Curtis R. Davis
*Attorney, Agent, or Firm*—Alexander J. McKillop; Charles J. Speciale; Marina V. Schneller

[57] ABSTRACT

An indium containing crystalline microporous material also containing a dehydrogenation component exhibits high selectivity for the aromatization of a normal paraffin to styrene, under dehydrocyclization conditions.

Group VIII metal-containing non-acidic crystalline microporous indium containing materials are highly selective catalysts for styrene production from n-octane.

8 Claims, No Drawings

STYRENE PRODUCTION

This is a continuation of copending application Ser. No. 138,473, filed on Dec. 28, 1987, now abandoned.

FIELD OF THE INVENTION

The invention pertains to a catalytic one-step transformation of octane to styrene. The catalytic composition for the transformation comprises a microporous crystalline indium containing material in combination with a strong dehydrogenation metal, such as platinum.

BACKGROUND OF THE INVENTION

Styrene $C_6H_5CH=CH_2$, is the common name for the simplest and by far the most important member of a series of unsaturated aromatic monomers. Sytrene is used extensively for the manufacture of plastics, including crystalline polystryene, rubber-modified impact polystyrene, acrylonitrilebutadiene-styrene terpolymer (ABS), styrene-acrylonitrile copolymer (SAN) and styrene-butadiene rubber (SBR).

Many different techniques have been investigated for the manufacture of styrene. The following methods have been used or seriously considered for commercial production: (1) dehydrogenation of ethylbenzene; (2) oxidation of ethylbenzene to ethylbenzene hydroperoxide, which reacts with propylene to give a-phenylethanol and propylene oxide, after which the alcohol is dehydrated to styrene; (3) oxidative conversion of ethylbenzene to a-phenylethanol via acetophenone and subsequent dehydration of the alcohol; (4) side-chain chlorination of ethylbenzene followed by dehydrochlorination; (5) side-chain chlorination of ethylbenzene, hydrolysis to the corresponding alcohols, followed by dehydration; and (6) pyrolysis of petroleum and recovery from various petroleum processes. The first two methods are the only commercially utilized routes to styrene: dehydrogenation of ethylbenzene accounts for over 90% of the total world production. Methods 4 and 5, involving chlorine, have generally suffered from the high cost of the raw materials and from the chlorinated contaminants in the monomer. Manufacture of styrene directly from petroleum streams (method 6) is difficult and costly.

The two commercially important routes to styrene are based on ethylbenzene produced by alkylation of benzene with ethylene.

Molecular sieves have been used in production of ethylbenzene which is subsequently dehydrogenated to produce the styrene. An ethylbenzene process was developed during the 1970s and was based on a synthetic zeolite catalyst, ZSM-5, developed by Mobil Oil Corporation. Although a number of zeolitic or molecular-sieve-type catalysts have been suggested for benzene alkylations with ethylene, most were characterized by very rapid build up of coke and, consequently, short-on-stream time. The Mobil catalyst represented a breakthrough in zeolite catalysis in that is combines high catalytic activity with relatively good resistance to coke formation. Total worldwide capacity based on the process was anticipated to be more than $3 \times 10^6$ t/yr by 1985.

Molecular sieves include naturally occurring and synthetic zeolites. Certain of these zeolites have been demonstrated to exhibit catalytic properties for various types of hydrocarbon conversions. Zeolites are ordered porous crystalline aluminosilicates having definite crystalline structure as determined by x-ray diffraction studies. Such zeolites have pores of uniform size which are uniquely determined by unit structure of the crystal. The zeolites are referred to as "molecular sieves" because interconecting channel systems created by pores of uniform pore size allow a zeolite to selectively absorb molecules of certain dimensions and shapes.

By way of background, one authority has described the zeolites structurally, as "framework" aluminosilicates which are based on an infinitely extending three-dimensional network of $AlO_4$ and $SiO_4$ tetrahedra linked to each other by sharing all of the oxygen atoms. Furthermore, the same authority indicates that zeolites may be represented by the empirical formula

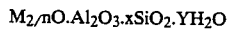

$$M_{2/n}O.Al_2O_3.xSiO_2.YH_2O$$

In the empirical formula, x is equal to or greater than 2, since $AlO_4$ tetrahedra are joined only to $SiO_4$ tetrahedra, and n is the valence of the cation designated M. D. Breck, ZEOLITE MOLECULAR SIEVES, John Wiley & Sons, New York p.5 (1974). In the empirical formula, the ratio of the total of silicon and aluminum atoms to oxygen atoms is 1:2. M was described therein to be sodium, potassium, magnesium, calcium, strontium and/or barium, which complete the electrovalence makeup of the empirical formula. One type of cation may be exchanged entirely or partially with another type of cation utilizing ion exchange techniques in a conventional manner. By means of such cation exchange, it has been possible to vary the properties of a given aluminosilicate by suitable selection of the cation. The cavities and pores are occupied by molecules of water prior to dehydration and/or possibly by organic species from the synthesis mixture in the as-synthesized materials. The prior art describes a variety of synthetic zeolites. These zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702886); zeolite ZSM-11 (U.S. Pat. No. 3,709,979) and zeolite ZSM-23 (U.S. Pat. No. 4,076,842), merely to name a few. The silicon/aluminum atomic ratio of a given zeolite is often variable. For example, zeolite X can be synthesized with silicon/aluminum atomic ratios of from 1 to 1.5, while that ratio in zeolite Y is from 1.5 to 3. In some zeolites, the upper limit of the silicon/aluminum atomic ratio is unbounded. ZSM-5 is one such example wherein the silicon/aluminum atomic ratio is at least 2.5 and up to infinity. U.S. Pat. No. 3,941,871, reissued as U.S. Pat. No. RE. 29,948, discloses a porous crystalline silicate made from a reaction mixture containing no deliberately added aluminum and exhibiting the x-ray diffraction pattern characteristic of ZSM-5 zeolites.

SUMMARY OF THE INVENTION

In accordance with the invention, styrene is produced by a catalytic transformation of octane in the presence of a catalyst composition comprising a microporous crystalline material and comprising 0.01 to 20 weight percent indium based on the microporous crystalline material and 0.01 to 30 weight percent (based on the weight of said material) of a strong hydrogenation/dehydrogenation metal. The process is a one-step conversion of normal-octane to styrene.

DETAILED DESCRIPTION OF THE INVENTION

Catalytic conversion of octane to styrene over a catalyst comprising a crystalline microporous material and 0.01 to 20 percent by weight indium and 0.01 to 30 weight percent of metal exhibiting dehydrogenation activity undertaken at octane dehydrocyclization conditions.

In a preferred embodiment the octane dehydrocyclization conditions include passing n-octane in the vapor state over the catalyst composition described. At atmospheric pressure, styrene will be produced at temperatures greater than about 400° C. At temperatures above about 500° C., good yields of styrene are obtained.

With all other apparent conditions held constant, the selectivity of the reaction to produce styrene appears to increase with increasing temperature. Runs to determine the efficacy of the process of the invention were undertaken by diluting the octane.

It was discovered that, with all apparent conditions held constant (including temperature) the selectivity of the reaction to produce styrene increases with decreasing partial pressure of normal-octane during contact with the catalyst. This was discovered by vaporizing the n-octane with nitrogen, a material inert to the thermodynamics of the dehydrocyclization. When another gas, hydrogen, which is apparently not inert to the thermodynamics favoring n-octane dehydrocyclization to produce styrene that same selectivity in terms of absolute styrene yields described in the examples was not realized.

The catalyst used comprises a hydrogenation/dehydrogenation metal and a non-acidic crystalline microporous indium containing material preferably a non-acidic crystalline microporous indium containing silicate. As catalysts these compositions can exhibit extremely high selectively for dehydrocyclization of n-octane to styrene.

The amount of dehydrogenation metal in the catalyst can range from 0.01 to 30 weight percent and prefereably 0.01 to 10 weight percent of the non-acidic crystalline microporous indium containing material. In a preferred embodiment, platinum is the hydrogenation/dehydrogenation metal. However, the hydrogenation/dehydrogenation metal can be any Group VIII metal including those of the platinum group, chromium and/or vanadium.

The indium content of the crystalline silicates can range from 0.01 to 20 weight percent. Practically, the indium content will range from 0.01 to 15 weight percent. In the embodiments described in the examples, indium content ranges from about 0.1 to about 10 weight percent.

The crystalline microporous indium containing materials of the invention are characterized by Si/Al ratios of at least 2. However, the silica:alumina ratio of the zeolite can be up to 1000, or greater. In specific embodiments the aluminum content of some of these materials is less than 0.1 weight percent.

The crystalline microporous indium containing material of the invention can contain other elements including boron, iron, chromium and gallium. The content of these other elements in the crystalline indium containing silicates can range from 0 to 10 weight percent.

The indium containing precursors of the invention, described herein, are crystalline in the sense that they are identifiable as isostructural with zeolites by X-ray powder diffraction pattern. The crystalline microporous indium containing material has an X-ray diffraction pattern which corresponds to a zeolite, SAPO, ALPO, etc. For example, indium silicate compositions of the invention have been made the crystal structure of which is that of ZSM-5, ZSM-11, ZSM-12 ZSM-23, ZSM-48, ZSM-50, zeolite Beta, ZSM-20, and SAPO-5. These are characterized by pore sizes up to about 8 Angstroms. The X-ray diffraction pattern and significant lines Tables of these materials have been described in the U.S. Patent literature. In a preferred embodiment the pore size of the microporous crystalline indium containing silicates ranges from about 5 to about 8 Angstroms.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be used on the following sorption properties (measured at room temperature for crystallites having a minimum dimension of 0.1 micron):

1. Small pore: $n-C_6/i-C_6$ sorption ratio greater than approximately 10.

2. Medium pore: $n-C_6/i-C_6$ is less than 10 and $n-C_6$/Mesitylene sorption ratio greater than approximately 5.

3. Large pore: $n-C_6$/Mesitylene sorption ratio less than approximately 5.

The compositions comprising hydrogenation/dehydrogenation metal combined with the crystalline indium containing silicates do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between and 10 and 60%. Alternatively, the non-acidic compositions will exhibit a pH of at least 6 when added to distilled deionized pH7 water maintained under inert (such as argon) atmosphere; by an inert atmosphere in this context it means an atmosphere free of $CO_2$. Typically, in these tests, 100 mg of catalyst was added to 30 ml. of distilled deionized water. Some compositions will exhibit a pH of at least 7.5 depending on the metal content.

When, as in embodiments herein, the crystalline indium dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison indium-free counterparts of those compositions catalyzed also hydrogenolysis of paraffins, e.g., to methane, as a major competing side reaction; and accordingly, the latter compositions exhibit decreased selectivity for the aromatization of paraffins but increased selectivity for $C_1$-$C_5$ paraffin production. Some of the aforementioned catalysts were screened for hexane and heptane aromatization at 538° C. in the presence of nitrogen diluent. The results are shown in Table A below in which the crystalline silicate employed exhibited the diffraction pattern of a ZSM-5.

TABLE A

Paraffin Aromatization over Non-Acidic Platinum Containing Crystalline Materials Isostructural With Pt/ZSM-5

| Support | Paraffin | Conversion | Benz. Sel.[c] | Tol. Sel. | C5-Sel |
|---|---|---|---|---|---|
| B/ZSM-5 | n-hexane | 52% | 31% | — | 12%[a] |
| " | " | 98% | 51% | 2% | 40%[a] |
| " | heptane | 56% | 56% | 8% | 7%[a] |
| " | " | 95% | 33% | 31% | 34%[a] |
| In/ZSM-5 | n-hexane | 60% | 81% | — | 1% |
| " | " | 99+% | 95% | — | 4% |
| " | heptane | 50% | — | 92% | 1% |
| " | " | 99% | — | 97% | 1% |
| Si/ZSM-5[d] | n-hexane | 58% | 69% | — | 18%[a] |
| " | " | 99% | 72% | — | 26%[a] |
| " | heptane | 34% | 45% | 17% | 14%[a] |
| " | " | 99% | 62% | 4% | 34%[a] |

[a]primarily methane.
[b]high silica/alumina ZSM-5.
[c]H2-free selectivity based on carbon The non-acidic platinum catalyst prepared from In/ZSM-5 provided much higher aromatics selectively than all the other catalysts examined. Benzene yields from hexane were as high as 95%, while heptane produced toluene in 97% yield (H2 free carbon base).

The other catalysts, including Pt/B-ZSM-5 and Pt/high silica:alumina ratio, did not show any appreciable acid activity, in that platinum chemistry dominated. Significant metal-catalyzed aromatization was observed; however hydrogenolysis to methane constituted a major competing side reaction. The highest toluene selectivity observed was 50–55%, and in most cases that selectivity was significantly lower. This is in sharp contrast to the aromatic product selectivity of the platinum-/In/ZSM-5. The cause for this difference in platinum behavior from the Pt/In-ZSM-5 catalyst is not clear.

SYNTHESIS OF THE COMPOSITIONS

The crystalline indium-materials can be made in various ways. Indium incorporation can be during synthesis or post-synthesis; and the materials can be prepared either by stepwise or simultaneous incorporation of the indium and the hydrogenation/dehydrogenation function. Alternatively, the reverse procedure can be applied in which the dehydrogenation function is first introduced with subsequent indium incorporation. Stepwise preparation includes techniques of cocrystallization, impregnation, or exchange. Crystallization can be undertaken in a two phase system described in commonly assigned Ser. No. 878,555, filed June 26, 1986. Other elements such as boron, iron chromium, gallium, can also be included. Simultaneous incorporation includes the combination of indium with the dehydrogenation/hydrogenation function during synthesis (i.e., crystallization) or simultaneously after synthesis of the crystalline material.

An indium free material can be treated with indium compounds at elevated temperatures. Such treatments can be conducted so that the source of indium is either in the gaseous (such as indium chloride) or the liquid phase including the aqueous phase (such as indium nitrate). Alternatively, an indium free crystalline reactant can simply be impregnated with indium source and then calcined at temperatures above 400° C.

The indium free reactant may have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by other than hydrogen, i.e., other than proton(s), and by other than hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

The non-acidic, crystalline, microporous, indium modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica.

EXAMPLES

Example 1

Synthesis of In-ZSM-5 was undertaken by the following procedure. A commercial silica gel (SPEX Ind.) with very low aluminum contamination was employed in the synthesis of In-ZSM-5. First, 0.85 g In(NO3)3 and 2.66 g NaOH pellets were dissolved in 180.2 g de-ionized water, then 5.64 g tetrapropylammonium bromide (TPABr) was dissolved in this basis solution. This solution was transferred o a 300 ml stainless steel autoclave, and 15.0 g of silica gel (SPEX) was added. The autoclave was then sealed and stirring and heating was begun. The hydrogel formed by this reaction mixture is described by the following mole ratios:

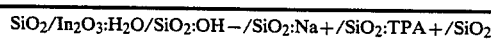

150:48:0.26:0.31:0.10

The hydrogel was reacted at 160 C for 2 days at a stirring rate of 400 rpm before quenching. The resultant crystalline product was filtered, washed, and dried. X-ray powder diffraction analysis showed the product to be 100% crystalline ZSM-5, when compared to the diffraction pattern of a conventional ZSM-5. Elemental analysis of the ZSM-5 product gave:

C=7.93 wgt %, N=0.74%, Na=0.56%, In=2.26%, Al 0.005%, SiO2-83.85%, ash=88.05%.

These results expressed in moles ratios were: C/N-=12.5; Moles/mole $In_2O_3$: $N_2O$=2.68, $Na_2O$=1.23, $Al_2O_3$=less than Platinum Incorporation into the crystalline material was undertaken as follows:

The as-synthesized zeolite was heated in nitrogen to 520° C. at 1° C./min. and held there for 6 hours. It was then calcined in air in a similar manner. The calcined zeolite analyzed for 41.05% Si, 2.21% In (Si/In2=152), and 120 ppm Al, and sorbed 10.4% n-hexane at 90° C. The calcined zeolite (3 g.) was stirred in a solution of 150 mg $Pt(NH_3)_4Cl_2$ in 100 ml water at room temperature overnight. After being washed, filtered and dried, the ion-exchanged zeolite was found to contain 0.41 meq $NH_3$/g ash, which is equivalent to 1.89% Pt on sample. The platinum tetramine zeolite was then calcined in oxygen to 350° C. at 0.5° C./min and held there for 1 hour. Elemental analysis indicated the presence of 1.85% Pt on the final catalyst.

Example 2

The Pt/In-ZSM-5 catalyzed conversion of n-octane in nitrogen yielded aromatics including styrene. Higher temperatures and greater dilution led to improved styrene yields as shown below:

| Octane Pressure | Temp °C. | Conversion | Styrene Yield |
|---|---|---|---|
| 10 torr | 450 | 99.3% | 4.8% |
| " | 500 | 95.4% | 17.9% |
| " | 538 | 98.4% | 33.2% |
| 1 torr | 550 | 99.4% | 64.3% |

In accordance with the invention, it is possible to produce styrene from normal-octane in a one step conversion.

In the following Examples A-J, other catalyst compositions which may be used in the invention are described.

Example A

Crystalline silicate products were produced containing indium and exhibiting characteristics X-ray diffraction patterns of structures corresponding to ZSM-5, ZSM-11, ZDM-12, ZSM-23, ZSM-48 and ZSM-50.

Table 1 compiles the composition ranges employed in the synthesis of a series of In/ZSM-5 products with widely varying indium content. Also shown in Table 1 is the synthesis of indium-containing silicates having X-ray pattern of ZSM-11, ZSM-12, ZSM-23, ZSM-48 and ZSM-50. The footnotes in Table 1 specify the $SiO_2$ sources and the organic directing agents employed in the synthesis.

The diffraction pattern for Sample of Run No. 8 showed it to be ZSM-5 of Sample from Run No. 13 to be ZSM-12 and of Sample from Run No. 6 to be ZSM-48.

Example B

The In/ZSM-5 of that run No. 12 was prepared as follows:

The source of the indium can be incorporated into the zeolitic silicate synthesis reaction mixture as a partial, or preferably as a complete substitute for sources of alumina (or boron) conventionally used in zeolite synthesis. In the embodiments described below the crystalline indium containing silicates were synthesized from crystallization reaction mixtures which contained no deliberately added sources of $Al_2O_3$.

TABLE 1

Crystallizations of Indium-Containing Zeolites
160° C.; Stirred 400 ppm

Mixture Composition (Mole Ratios)

| Run No. | $\frac{SiO_2}{In_2O_3}$ | $\frac{H_2O}{SiO_2}$ | $\frac{OH^-}{SiO_2}$ | $\frac{NA^+}{SiO_2}$ | $\frac{R}{SiO_2}$ | Time, Days | Zeolite Product |
|---|---|---|---|---|---|---|---|
| 1[a] | 500 | 48 | 0.26 | 0.27 | 0.10[c] | 3 | ZSM-5 |
| 2[b] | 500 | 48 | 0.26 | 0.27 | 0.10[c] | 3 | ZSM-5 |
| 3[a] | 300 | 48 | 0.26 | 0.28 | 0.10[c] | 3 | ZSM-5 |
| 4[b] | 300 | 48 | 0.26 | 0.28 | 0.10[c] | 1 | ZSM-5 |
| 5[d] | 300 | 48 | 0.26 | 0.28 | 0.20[b] | 1 | ZSM-5 |
| 6[b] | 200 | 48 | 0.26 | 0.30 | 0.10[e] | 4 | ZSM-48 |
| 7[b] | 200 | 48 | 0.26 | 0.30 | 0.10[f] | 4 | ZSM-11 |
| 8[b] | 150 | 48 | 0.26 | 0.31 | 0.10[c] | 2 | ZSM-5 |
| 9[b] | 150 | 48 | 0.26 | 0.31 | 0.10[c] | 2 | ZSM-5 |
| 10[b] | 150 | 48 | 0.26 | 0.31 | 0.10[c] | 2 | ZSM-5 |
| 11[b] | 150 | 48 | 0.26 | 0.31 | 0.10[c] | 3 | ZSM-5 |
| 12[b] | 150 | 48 | 0.26 | 0.31 | 0.10[c] | 2 | ZSM-5 |
| 13[b] | 100 | 48 | 0.26 | 0.34 | 0.08[g] | 3 | ZSM-12 |
| 14[h] | 76 | 48 | 0.26 | 0.59 | 0.10[c] | 6 | ZSM-5 |
| 15[i] | 70 | 40 | 0.20 | 0.23 | 0.10[c] | 3 | ZSM-5 |
| 16[b] | 70 | 40 | 0.26 | 0.37 | 0.10[c] | 3 | ZSM-5 |
| 17[a] | 60 | 48 | 0.26 | 0.39 | 0.10[c] | 3 | ZSM-5 |
| 18[b] | 150 | 40 | 0.20 | 0.25 | 0.10[j] | 3 | ZSM-23 |
| 19[b] | 300 | 40 | 0.20 | 0.23 | 0.10[j] | 3 | ZSM-23 |

TABLE 1-continued

Crystallizations of Indium-Containing Zeolites
160° C.; Stirred 400 ppm

| | Mixture Composition (Mole Ratios) | | | | | | |
|---|---|---|---|---|---|---|---|
| Run No. | $\frac{SiO_2}{In_2O_3}$ | $\frac{H_2O}{SiO_2}$ | $\frac{OH^-}{SiO_2}$ | $\frac{NA^+}{SiO_2}$ | $\frac{R}{SiO_2}$ | Time, Days | Zeolite Product |
| 20[b] | 300 | 40 | 0.20 | 0.23 | 0.10[k] | 3 | ZSM-50 |

[a]Silica source is tetraethylorthosilicate ($Et_4SiO_4$)
[b]Silica source is SPEX Industries precipitated $SiO_2$
[c]R = $TPA^+$
[d]Silica source is DeGussa fumed $SiO_2$
[e]R = DIQUAT-6 = $(CH_3)_3\overset{+}{N}(CH_2)_6\overset{+}{N}(CH_3)_3$
[f]R = $TBA^+$

[g]R = 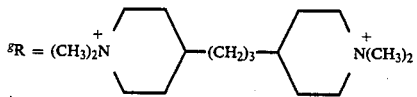

[h]Q-brand sodium silicate
[i]Silica source is kieselsaure precipitated $SiO_2$
[j]R = DIQUAT-7 = $(CH_3)_3\overset{+}{N}(CH_2)_7\overset{+}{N}(CH_3)_3$
[k]R = Dibenzyldimethylammonium ion A commercial silica gel (SPEX Ind.) with very low aluminum contamination was employed in the synthesis of In-ZSM-5. First, 0.85 g $In(NO_3)_3$ and 2.66 g NaOH pellets were dissolved in 180.2 g de-ionized water, then 5.64 g of tetrapropylammonium bromide (TPABr) was dissolved in this basis solution. This solution was transferred to a 300 ml stainless steel autoclave, and 15.0 g of silica gel (SPEX) was added. The autoclave was then sealed and stirring and heating was begun. The hydrogel formed by this reaction mixture is described by the following mole ratios:

$SiO_2/In_2O_3$:$H_2O/SiO_2$:$OH^-/SiO_2$:$Na+/SiO_2$:$TPA+/SiO_2$
150:48:0.26:0.31:0.10

Table 2A is a compilation of chemical analyses of some of our indium-containing products. These products vary in indium content from 0.36–5.20 wt% In. The formulas of the zeolite products are expressed in Table 2 as a ratio of oxides per mole of $In_2O_3$.

The hydrogel was reacted at 160° C. for 2 days at a stirring rate of 400 rpm before quenching. The resultant crystalline product was filtered, washed, and dried. X-ray powder diffraction analysis showed the product to be 100% crystalline ZSM-5, when compared to the diffraction pattern of a conventional ZSM-5. Elemental analysis of the ZSM-5 product gave: C=7.93 wgt %, N=0.74%, Na=0.56%, In=2.26%, Al 0.005%, $SiO_2$=83.85%, Ash=88.05%.

These results expressed in mole ratios were: C/N=12.5; Moles/mole $In_2O_3$: $N_2O$=2.68, $Na_2O$=1.23, $Al_2O_3$=0.009, Platinum incorporation was undertaken as follows: The as-synthesized zeolite was heated in nitrogen to 520° C. at 1C/min and held there for 6 hours. It was then calcined in air in a similar manner. The calcined zeolite analyzed for 41.05% Si, 2.21% In (Si/In2=152), and 120 ppm Al, and sorbed 10.4% n-hexane at 90C. The calcined zeolite (3 g) was stirred in a solution of 150 mg $Pt(NH_3)_4Cl2$ in 100 ml water at room temperature overnight. After being washed, filtered and dried, the ion-exchanged zeolite was found to contain 0.41 meq $NH_3$/g ash, which is equivalent to 1.89% Pt on sample. The platinum tetramine zeolite was then calcined in oxygen to 350C at 0.5C/min and held there for 1 hour. Elemental analysis indicated the presence of 1.85% Pt on the final catalyst.

TABLE 2A

Analyses of Some Indium-Containing Zeolitic Silicate Products

| Sample Run from No. | Weight Percent | | | | | | | Moles C Moles N | Moles per Mole $In_2O_3$ | | | |
|---|---|---|---|---|---|---|---|---|---|---|---|---|
| | C | N | Na | In | $SiO_2$ | $Al_2O_3$ | Ash | | $N_2O$ | $Na_2O$ | $Al_2O_3$ | $SiO_2$ |
| 15 | 6.96 | 0.66 | 3.28 | 5.20 | 62.47 | 0.070 | 85.34 | 12.3 | 1.04 | 3.15 | 0.03 | 46 |
| 14 | 6.74 | 0.43 | 2.64 | 4.19 | 69.94 | 0.24 | 86.20 | 18.3 | 0.84 | 3.14 | 0.13 | 64 |
| 16 | 7.02 | 0.56 | 0.79 | 3.48 | 76.45 | 0.035 | 84.78 | 14.6 | 1.32 | 1.13 | 0.02 | 84 |
| 13 | 6.01 | 0.61 | 0.65 | 2.79 | 81.83 | 0.031 | 91.79 | 11.2 | 1.79 | 1.16 | 0.025 | 112 |
| 9 | 8.02 | 0.71 | 0.98 | 2.11 | 74.85 | 0.078 | 88.05 | 13.6 | 2.36 | 2.29 | 0.06 | 132 |
| 8 | 8.01 | 0.68 | 1.48 | 2.14 | 74.64 | 0.11 | 88.72 | 13.7 | 2.61 | 3.45 | 0.11 | 133 |
| 12 | 7.93 | 0.74 | 0.56 | 2.26 | 83.85 | 0.005 | 88.05 | 12.4 | 2.68 | 1.23 | 0.009 | 142 |
| 10 | 8.37 | 0.81 | 1.83 | 1.92 | 73.14 | 0.025 | 88.36 | 12.0 | 3.46 | 4.76 | 0.03 | 146 |
| 11 | 8.22 | 0.62 | 0.54 | 1.49 | 82.14 | 0.031 | 85.96 | 15.5 | 3.41 | 1.81 | 0.05 | 211 |
| 6 | 4.58 | 0.79 | 0.48 | 1.46 | 86.70 | 0.029 | 91.86 | 6.7 | 4.44 | 1.64 | 0.045 | 227 |
| 7 | 8.66 | 0.51 | 0.44 | 0.96 | 82.29 | 0.013 | 89.43 | 19.8 | 4.36 | 2.29 | 0.045 | 328 |
| 2 | 8.12 | 0.69 | 0.40 | 0.36 | 78.05 | 0.083 | 85.69 | 13.7 | 15.7 | 5.55 | 0.52 | 830 |

A standard test based on hexane conversion at 1000° F. indicated an apparent hexane conversion activity between 200 and 500, with a very high benzene selectivity (60%). At very high hexane conversions (99%), benzene was formed in over 94% yield. Similarly, n-heptane yielded 96% toluene. Similarly, n-heptane yielded 96% toluene. Consistent with the non-acidic nature of this platinum catalyst, n-octane yielded in addition to styrene, ethylbenzene and ortho-xylene, 2-methylheptane produced mostly meta-xylene, and 3-methylheptane formed mainly ethylbenzene, para-, and ortho-xylene.

Example C

In EXAMPLE A, zeolitic silicate was made using In(NO₃)₃ in the crystallization reaction mixture as in the Example below. Here, indium was incorporated post-synthesis; in a subsequent step platinum was ion-exchanged onto the zeolite.

In this example, a high silica/alumina (10,000) ZSM-11 was calcined in nitrogen and then in air at 538° C. InCl₃ vapors were passed through the zeolite in a stream of nitrogen, while it was heated to 500° C. at 10C/min. The zeolite was maintained at 500° C. for 1.5 hours. After cooling, the catalyst was added to 200 ml 1M NH₄Cl adjusted to pH 9.5 with NH₄OH. The mixture was stirred for 20 minutes at room temperature, and then filtered. The zeolite was then reexchanged for 3 hours with 1M NH₄Cl adjusted to pH 7.6. The rmogravimetric analysis indicated the presence of 0.325 meq/g ammonium ion in the zeolite.

Platinum was incorporated by ion exchange with Pt(NH₃)₄Cl₂ at room temperature. The platinum zeolite was then calcined in oxygen to 350C at 0.5C/min.

The "non-acidic" nature of the catalyst was confirmed by its ability to aromatize n-heptane to toluene in high yield. At about 500° C. (up to about 538° C.) and 30 torr heptane in nitrogen, toluene was formed in 94% selectivity at a conversion level of greater than 90%.

Example D

The ZSM-5-type borosilicate was synthesized at 170° C. from a mixture of 12.4 g high purity silica (SPEX), 105 g 20% TEA hydroxide, and 0.8 g boric acid. The as-synthesized zeolite was then calcined in nitrogen and then in air at 520° C. The calcined zeolite contained 41.39% Si, 0.015% Al, and 0.44% B.

Two grams of the calcined borosilicate was impregnated with 135 mg In(NO₃)₃, and calcined in air at 500° C. for 2 hours. 1.8 g of this material was then ion-exchanged with 28 mg Pt(NH₃)₄Cl₂ in 100 ml water at room temperature. TGA analysis in hydrogen indicated the presence of 0.18 meq N/g equivalent to 0.87% Pt. The platinum-exchanged zeolite was then calcined in oxygen to 350° C. at 0.5° C./min.

The catalyst activity of the foregoing composition was examined The "non-acidic" nature of the catalyst was confirmed by its ability to aromatize n-heptane to toluene in high yield. At 500° C. and 30 torr heptane in nitrogen, toluene was formed in 95% yield. Furthermore, the small amounts of both methane and propane produced were exceeded by the ethane formed, indicative of the low hydrogenolysis and acid activity of the catalyst.

| % Conversion | % C1 | % C2 | % Benzene | % Toluene (Selectivity) |
|---|---|---|---|---|
| 96 | 0.4 | 0.6 | 1.3 | 92 (96%) |
| 99 | 0.5 | 1.0 | 1.5 | 95 (96%) |

Example E

Indium-containing zeolite ZSM-20 was synthesized by the following procedure:

12.75 grams of sodium aluminate (NaAlO₂) and 6.02 grams indium nitrate were dissolved in 57.96 grams of deionized water. After the solid ingredients dissolved, 484.1 ml of 2.88 N tetraethylammonium hydroxide (TEAOH) was added to the solution. The resulting solution was not stirred into 312.5 grams of tetraethylorthosilicate. This solution was kept stirring for one hour until the hydrolysis reaction was complete. The resulting hydrogel was now transferred to a one-liter polypropylene bottle.

The polypropylene bottle was loosely capped and placed into a steambox (100° C.) to promote the crystallization of the zeolite. The next morning the bottle was removed from the steambox and the bottle cap was now closed tightly. The bottle was shaken vigorously, then replaced into the steambox. The reaction mixture for the initial hydrogel formed for the synthesis of the indium-containing ZSM-20 can be described by the following set of mole ratios:

| | |
|---|---|
| SiO₂/In₂O₃ | 150 |
| H₂O/SiO₂ | 10 |
| OH⁻/SiO₂ | 0.9 |
| Na⁺/SiO₂ | 0.09 |
| TEA⁺/SiO₂ | 0.93 |
| SiO₂/Al₂O₃ | 30 |

Samples of the solid product were removed daily from the polypropylene bottle for X-ray diffraction (XRD) analysis to determine the product crystallinity. XRD analysis showed that the ZSM-20 crystallization was complete in 14 days. The polypropylene bottle was removed from the steambox, and the solid product was filtered on a B chner funnel. After filtration, the product zeolite was boiled in de-ionized water and again filtered and dried under an infrared heat lamp. After drying, a sample of the product was submitted for XRD and chemical analysis. XRD analysis showed the product to be zeolite ZSM-20. The chemical analysis for the indium-containing ZSM-20 was:

| | | Weight Percent | | | | |
|---|---|---|---|---|---|---|
| C | N | Na | In | SiO₂ | Al₂O₃ | Ash |
| 10.0 | 1.2 | 3.0 | 3.08 | 58.5 | 11.4 | 75.1 |

| which gives: | | | | |
|---|---|---|---|---|
| Moles C / Moles N | | Moles per Mole In₂O₃ | | |
| | N₂O | Na₂O | Al₂O₃ | SiO₂ |
| 9.7 | 3.19 | 4.86 | 8.33 | 72.7 |

Example F

Indium-containing zeolite Beta was synthesized in the following manner:

5.95 grams of sodium aluminate and 4.68 grams of indium nitrate were dissolved in 85.14 grams of de-ionized water. After the salts dissolved, 105.0 ml of 3.1 N TEAOH was added to the solution. The resulting solution was transferred to a 300ml stainless-steel autoclave.

Now 46.67 grams of solid silica gel (SPEX Industries) was pored into the autoclave, the autoclave was sealed and stirring and heating begun immediately. The reaction was carried out at 160° C. with stirring (400 rpm).

The initial reaction mixture for the synthesis of indium-containing zeolite Beta can be described by the mole ratios:

| | |
|---|---|
| SiO₂/In₂O₃ | 90 |
| H₂O/SiO₂ | 12 |
| OH⁻/SiO₂ | 0.40 |
| Na⁺/SiO₂ | 0.09 |
| TEA⁺/SiO₂ | 0.46 |

-continued

| | |
|---|---|
| SiO$_2$/Al$_2$O$_3$ | 30 |

After 4 days the autoclave was quenched in a water plus ice bath to terminate the reaction. The solid product was filtered, boiled in water and again filtered. XRD analysis showed the crystalline product to be zeolite Beta. Chemical analysis of the indium-containing zeolite Beta product gave the following results:

| Weight Percent | | | | | | |
|---|---|---|---|---|---|---|
| C | N | Na | In | SiO$_2$ | Al$_2$O$_3$ | Ash |
| 10.84 | 1.71 | 1.4 | 2.5 | 69.8 | 4.2 | 79.92 | which gives:

| Moles C / Moles N | | Moles per Mole In$_2$O$_3$ | | |
|---|---|---|---|---|
| | N$_2$O | Na$_2$O | Al$_2$O$_3$ | SiO$_2$ |
| 7.4 | 5.61 | 2.79 | 3.78 | 62.8 |

Example G

Indium-containing crystalline aluminophosphate molecular sieve ALPO-5 was synthesized as follows:

23.1 grams of concentrated phosphoric acid (86.3% H$_3$PO$_4$) was diluted with 30.0 grams of de-ionized water. Now 10.0 grams of Kaiser alumina was stirred into this acid solution and the mixture was digested for 45 minutes at 90°C with continuous stirring. After the digestion period a solution containing 1.18 grams of indium nitrate dissolved in 41.0 grams of de-ionized water was stirred into the gel. Finally, 37.0 grams of 40% wt. TEAOH solution was stirred into the gel and stirring continued until a uniform gel was produced. This gel was not transferred to a 300 ml stainless-steel autoclave. The resulting reaction mixture hydrogel can be described by the following mole ratios:

| | |
|---|---|
| P$_2$O$_5$/Al$_2$O$_3$ | 1.0 |
| H$_2$O/Al$_2$O$_3$ | 59 |
| H$^+$/Al$_2$O$_3$ | 7.2 |
| In$_2$O$_3$/Al$_2$O$_3$ | 0.02 |
| TEA$^+$/Al$_2$O$_3$ | 1.0 |

The autoclave was sealed and heated and stirring began immediately. The reaction was carried out at 160° C. with stirring (400 rpm).

After 4 days the autoclave was quenched in a water +ice bath to terminate the crystallization. The solid product was filtered, boiled in water and filtered again. After drying the product, XRD analysis showed the material to be crystalline aluminophosphate designated by Union Carbide as ALPO-4. Chemical analysis of the indium-containing ALPO-5 gave:

| Weight Percent | | | | | | |
|---|---|---|---|---|---|---|
| C | N | Na | P | Al | In | Ash |
| 6.66 | 0.84 | 0.48 | 21.05 | 16.01 | 1.44 | 89.45 | which gives:

| Moles C / Moles N | | Moles per Mole In$_2$O$_3$ | | |
|---|---|---|---|---|
| | N$_2$O | Na$_2$ | P$_2$O$_5$ | Al$_2$O$_3$ |
| 9.2 | 4.78 | 1.66 | 54.2 | 47.3 |

Example H

Indium-containing crystalline silicoaluminophosphate molecular sieve SAPO-5 was synthesized in a manner analogous to EXAMPLE G:

46.2 grams of concentrated phosphoric acid (86.3% H$_3$PO$_4$) was first diluted with 60.0 grams of de-ionized water then 20.0 grams of Kaiser alumina was added to the solution. This mixture was now digested on a hot plate at 90° C. for 45 minutes, with continuous stirring. At the end of the digestion period, a solution containing 2.36 grams of indium nitrate dissolved in 82.0 grams of de-ionized water was stirred into the gel. Next 74.0 grams of 40% wt TEAOH solution was stirred into the gel. This mixture was now stirred at room temperature until a uniform hydrogel was produced. The resulting hydrogel was transferred to a one-liter stainless-steel autoclave. Before sealing the autoclave, 2.04 grams of tetraethylorthosilicate was transferred to the autoclave. The autoclave was then sealed and heating and stirring was begun immediately. The resulting reaction mixture can be described by the following mole ratios:

| | |
|---|---|
| P$_2$O$_5$/Al$_2$O$_3$ | 1.0 |
| H$_2$O/Al$_2$O$_3$ | 59 |
| H$^+$/Al$_2$O$_3$ | 7.2 |
| In$_2$O$_3$/Al$_2$O$_3$ | 0.02 |
| SiO$_2$O$_3$/Al$_2$O$_3$ | 0.10 |
| TEA$^+$/Al$_2$O$_3$ | 1.0 |

The crystallization of the indium-containing SAPO was carried out at 150° C. with stirring (400 rpm).

At the end of 4 days the autoclave was quenched in a water+ice bath to terminate the crystallization. The solid product was filtered, boiled in water, and re-filtered. After drying under a heat lamp, XRD analysis showed that the reflection lines for the product corresponded to silicoaluminophosphate SAPO-5, a Union Carbide designation for this material.

Chemical analysis of the indium-containing SAPO-5 gave:

| Weight Percent | | | | | | | |
|---|---|---|---|---|---|---|---|
| C | N | Na | P | Al | In | Si | Ash |
| 6.32 | 0.60 | 0.48 | 19.88 | 15.71 | 1.45 | 0.66 | 85.00 | which gave

| Moles C / Moles N | | Moles per Mole In$_2$O$_3$ | | | |
|---|---|---|---|---|---|
| | N$_2$O | Na$_2$O | P$_2$O$_5$ | Al$_2$O$_3$ | SiO$_2$ |
| 12.3 | 3.39 | 1.65 | 50.8 | 46.1 | 3.7 |

Example I

Platinum incorporation into the indium-containing silicate of ZSM-5 structure was carried out by direct addition of a platinum compound to the zeolite synthesis reaction mixture as follows:

A solution was prepared by dissolving 2.00 grams of indium nitrate and 13.07 grams of NaOH pellets in 710.28 grams of de-ionized water. After the solids dissolved, 26.6 grams of tetrapropylammonium bromide (TPABr) was dissolved in the solution. Finally 1.29 grams of platinum tetraaminenitrate [Pt(NH$_3$)$_4$(NO$_3$)$_2$] was dissolved in the solution, and the solution was transferred to a one-liter stainless-steel autoclave. Before sealing the autoclave, 66.67 grams of commercial silica gel (SPEX Industries) was poured into the autoclave. The autoclave was then sealed and heating and stirring was begun immediately. The reaction mixture hydrogel can be described by the following mole ratios:

| | |
|---|---|
| $SiO_2/In_2O_3$ | 300 |
| $H_2O/SiO_2$ | 40 |
| $OH^-/SiO_2$ | 0.30 |
| $Na^+/SiO_2$ | 0.33 |
| $TPA^+/SiO_2$ | 0.10 |
| $SiO_2/Pt$ | 300 |

The crystallization was carried out at 170° C. with stirring (400 rpm).

After 4 days the autoclave was quenched in a water- +ice bath to terminate the crystallization. In the usual manner the solid product was filtered, boiled in water, and finally filtered again before drying under a heat lamp. XRD analysis of the solid product showed the material to be crystalline zeolite ZSM-5.

Chemical analysis of the indium-containing ZSM-5 product gave:

| | | | Weight Percent | | | | |
|---|---|---|---|---|---|---|---|
| C | N | Na | In | Pt | $SiO_2$ | $Al_2O_3$ | Ash |
| 8.27 | 0.74 | 1.3 | 1.1 | 0.52 | 82.7 | 0.0265 | 85.05 | which gave:

| Moles C / Moles N | | Moles per Mole $In_2O_3$ | | | |
|---|---|---|---|---|---|
| | $N_2O$ | $Na_2O$ | $Al_2O_3$ | $SiO_2$ | Pt |
| 13.1 | 5.52 | 5.90 | 0.05 | 288 | 0.55 |

Example J

A boron-containing zeolite beta was synthesized and then calcined to remove the organic template, by heating first in $N_2$ 25°-530° at 10/min and held 6 hrs. then in air in $N_2$ 25°-530° at 10/min. and held 6 hours.

25g of the calcined zeolite was ion-exchanged with 750 mg $Pt(NH_3)_4Cl_2$ in 400 ml $H_2O$ at room temperature overnight. The dried material was then calcined in flowing oxygen (100 cc/min.) 25°-350° at 1/2°/min. and held 1 hour.

10g of the calcined Pt-containing zeolite was then treated with 0.9g $In(NO_3)_3$ $H_2O$ in 200 ml $H_2O$ at RT overnight.

The zeolite was filtered and washed.

The In-containing Pt/zeolite was added to 150ml $H_2O$ and titrated to pH 9.0 with 0.5 MCsOH (1½ hrs). The material was filtered, washed, and dried. The final product contained 0.76% Pt, 11% Cs, 1.1% In, and 0.08% B.

Example K

The synthesis of a binary oxide zeolite having the structure of ZSM-5 was carried out in the two-phase system as in Ser. No. 878,555 filed June 26, 1986. The aqueous phase of the two-phase system comprised 2.8 g $In(NO_3)_3xH_2O$ dissolved in 35 g water to which was added 63 g TPAOH (40% in $H_2O$). Constituting the organic phase was 77.0 g $Si(OCH_3)_4$ dissolved in 35 g of 1-hexanol. The mixture was nucleated at 180° C. for 24 hours and crystallized at 200° C. for 144 hours. The final product was filtered and washed. The X-ray diffraction pattern of the dried material provided it to be well-crystallized ZSM-5.

The sample was ammonium-exchanged (1 M $NH_4Cl$, twice, 60° C., 20 ml/g zeolite) and calcined. The chemical composition of the ash of a 1000° C. calcined sample was 79.3 wt. % $SiO_2$ and 1.5 wt. % $In_2O_3$. The ash residue also contained a small quantity, i.e. 85 ppm, of aluminum.

Temperature-programmed desorption of ammonia indicated an exchange capacity of 0.09 meq/g for the product of this example. The Si/In ratio from TPAD was 190.5. The sample had an Alpha Value of 1.0.

The particle size of the product from this example was about 0.2 microns. The particles were made of pure single crystals with almost cubic appearance.

Example L

The synthesis of Example K was repeated, except that the mixture contained 3.6 g $In(NO_3)_3.xH_2O$ in the aqueous phase. The product material was filtered and dried. It had the same characteristic ZSM-5 X-ray lines as the product of Example K. The material was calcined and ammonium-exchanged as described in Example K. The chemical composition of the ash of a 1000° C. calcined sample was 78.2 wt. % $SiO_2$ and 3.1 wt. % $In_2O_3$. The ash residu also contained a small quantity, i.e. 180 ppm, of aluminum.

Temperature-programmed desorption of ammonia indicated an exchange capacity of 0.21 meq/g for the product of this example. The Si/In ratio from TPAD was 77.9. The sample had an Alpha Value of 2.5.

The particle size of the product from this example was about 0.2 microns. The particles were made of crystals with almost cubic appearance. There were no impurities present.

Examples M-Q

The synthesis of Example K was repeated, except that the mixtures contained varying amounts of $In(NO_3)_3.xH_2O$. Five preparations were made, with the following compositions:

| Example | M | N | O | P | Q |
|---|---|---|---|---|---|
| Aqueous Phase (g) | | | | | |
| $H_2O$ | 40.0 | 40.0 | 35.0 | 40.0 | 40.0 |
| $In(NO_3)_3x3H_2O$ | 0.9 | 7.2 | 1.8 | 1.8 | 3.6 |
| TPAOH, 40% | 63.0 | 63.0 | 63.0 | 63.0 | 63.0 |
| Organic Phase (g) | | | | | |
| 1-Hexanol | 60.0 | 60.0 | 35.0 | 60.0 | 60.0 |
| $Si(OCH_3)_4$ | 77.0 | 77.0 | 77.0 | 77.0 | 77.0 |

The product materials were filtered and dried. They had the same characteristic X-ray lines as ZSM-5. The materials were calcined and ammonium-exchanged as in Example K. Their properties were as follows:

| Example | M | N | O | P | Q |
|---|---|---|---|---|---|
| $SiO_2$, wt. % | 84.0 | 77.5 | 80.5 | 76.7 | 82.5 |
| $In_2O_3$, wt. % | 0.67 | 5.1 | 1.58 | 1.31 | 2.92 |
| Al, ppm | 105 | 65 | 130 | 85 | 60 |
| Exchange Capacity, meq/g | 0.09 | 0.17 | 0.17 | 0.12 | 0.21 |
| Si/In (from TPAD) | 193 | 99 | 95 | 138 | 77 |
| Alpha Value | 1.5 | 1.6 | 1.0 | 1.0 | n.d. |
| Particle size | 2000 A | 1 micr | 2000 A | 2000 A | 2000 A |

What is claimed is:

1. A process for producing styrene from n-octane comprising contacting n-octane over a catalyst composition, under conditions effective to dehydrocyclize n-octane to styrene, wherein the catalyst composition comprises a non-acidic crystalline microporous material containing indium and a dehydrogenation/hydrogenation metal, wherein the indium content of the composition ranges from 0.01 to 20 weight percent; wherein the dehydrogenation/hydrogenation metal comprises 0.01 to 30 weight percent and, by said contacting, producing styrene.

2. The process of claim 1, wherein said material is a silicate.

3. The process of claim 2, wherein the silicate has the X-ray diffraction pattern of ZSM-5.

4. The process of claim 1, wherein said n-octane is admixed with an inert diluent under said conditions of contacting.

5. The process of claim 1, wherein said n-octane is in the vapor state.

6. The process of claim 3, wherein said n-octane is in the vapor state.

7. The process of claim 1, wherein said conditions include a temperature of at least about 400° C.

8. The process of claim 1, wherein said conditions include a temperature of at least about 500° C.

* * * * *